United States Patent [19]

Dingwall et al.

[11] 4,398,033

[45] Aug. 9, 1983

[54] 4-CHLORO-4-CHLOROMETHYLOXETAN-2-ONE AND A PROCESS FOR ITS PRODUCTION

[75] Inventors: John G. Dingwall, Riehen, Switzerland; Brian Tuck, Stockport, England

[73] Assignee: Ciba-Geigy Corporation, Ardsley, N.Y.

[21] Appl. No.: 355,498

[22] Filed: Mar. 8, 1982

[30] Foreign Application Priority Data

Mar. 17, 1981 [GB] United Kingdom ............... 8108236

[51] Int. Cl.$^3$ ............................................. C07D 305/12
[52] U.S. Cl. ................................. 549/329; 204/158 R
[58] Field of Search ..................... 549/329; 204/158 R

[56] References Cited

U.S. PATENT DOCUMENTS 4,363,923  12/1982  Dingwall et al. ................... 549/329

OTHER PUBLICATIONS

Fieser et al., Reagents for Org. Syn., vol. 2, p. 394.
Hurd et al., J.A.C.S., 1940, p. 1147.
Kunihiko et al., Chem. Abs. 86:139408h.

*Primary Examiner*—Jane T. Fan
*Attorney, Agent, or Firm*—Michael W. Glynn

[57] ABSTRACT

The new compound 4-chloro-4-chloromethyloxetan-2-one can be prepared by reacting diketene with sulphuryl chloride under conditions in which free radicals are formed.

The 4-chloro-4-chloromethyloxetan-2-one exhibits antimicrobial activity. It is also useful as an intermediate, for example for the production of pigments and dyestuffs.

12 Claims, No Drawings

4-CHLORO-4-CHLOROMETHYLOXETAN-2-ONE AND A PROCESS FOR ITS PRODUCTION

The present invention relates to the new compound 4-chloro-4-chloromethyloxetan-2-one, and a process for its production.

The present invention provides the new compound 4-chloro-4-chloromethyloxetan-2-one having the formula:

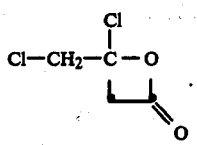

It is well known that chlorination of diketene with molecular chlorine gives $ClCH_2COCH_2COCl$:

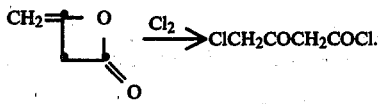

In 1940, before the precise structure of diketene had been determined, Hurd and Abernethy [JACS 62, 1147 (1940)] suggested that 4-chloro-4-chloromethyloxetan-2-one might be an intermediate in the formation of $ClCH_2COCH_2COCl$ by the chlorination of diketene with chlorine in carbon tetrachloride. On the basis of other evidence they then rejected this hypothesis.

According to the invention 4-chloro-4-chloromethyloxetan-2-one is prepared by the free radical chlorination of diketene with sulphuryl chloride. The compound is a stabe distillable liquid. It was further shown that it is unreactive under the conditions employed by Hurd and Abernethy for the chlorination or diketene, viz. carbon tetrachloride solution, chlorine, 0° C. and thus the possibility of 4-chloro-4-chloromethyloxetan-2-one being an intermediate in the ionic chlorination of diketene to give γ-chloroacetoacetyl chloride can be completely discounted both theoretically and practically.

According to the present invention, there is also provided a process for producing 4-chloro-4-chloromethyloxetan-2-one comprising reacting diketene with sulphuryl chloride under conditions in which free radicals are formed.

Thus, the reaction is carried out so that the free radicals are formed by the application to the reaction mixture of ionising radiation or of ultraviolet radiation. Alternatively, the reaction may be effected in the presence of a chemical compound capable of forming free radicals for instance:

(i) Organic peroxides, suitable examples of which include: t-butyl peracetate, t-butyl perbenzoate, acetylperoxide, benzoylperoxide, di-isopropylperdicarbonate, di-t-butylcyclohexylperdicarbonate, di-t-butylperoxide, t-butylhydroperoxide.

(ii) Inorganic peroxy compounds, suitable examples of which are hydrogen peroxide and ammonium persulphate.

(iii) Organic azo compounds such as azobisisobutyronitrile and azobisisopropane.

(iv) Combination of (i) or (iii) with ultraviolet radiation.

(v) Combination (i) or (ii), with a metal ion catalyst, suitable examples of which include Cu, V, Fe, and Ti to give a radical-producing redox-system e.g.

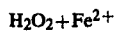

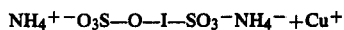

The compounds capable of forming free radicals may be used, with advantage, in catalytic amounts, e.g. from 0.1 to 10 mol.%, preferably from 1 to 5 mol.%, based on the amount used of diketene. If desired, the reaction may be carried out in the presence of a solvent which is inert under the reaction conditions. Examples of such inert solvents include petroleum ether, benzene, chlorobenzene and, preferably, carbon tetrachloride. The temperature at which the reaction is effected will depend on the method used to produce free radicals. In general, however, the reaction is conveniently effected within the range of from 0° to 100° C. The reaction may be performed batchwise or in a continuous manner, such as in a cascade reactor.

The compound of formula I exhibits antimicrobial activity within the concentration ranges up to 1000 μg/ml. against a range of organisms. In particular, the compound of formula I controls the growth of bacteria and fungi, e.g. *Staphylococcus aureus, Escherichia coli, Salmonella typhi, Proteus vulgaris, Pseudomonas aeruginosa, Candida albicans* and *Aspergillus niger* at low concentration.

The compound of formula I can be applied as an antimicrobial in pure form or as a concentrated of dilute solution in an inert solvent which may be miscible or immiscible with aqueous systems. Examples of inert solvents include hydrocarbons, e.g. kerosene; aromatic solvents such as xylene; ketones e.g. acetone; or glycol ethers e.g. 1,2-dimethoxyethane, 1,2-diethoxyethane, diethylene glycol dimethyl ether and diethylene glycol diethyl ether. Such solutions may optionally contain emulsifying or dispersing agents and may be optionally stabilised with alkali- or alkaline earth metal carbonates. It is also possible to apply the compound of formula I in admixture with solid carriers. If desired, the compound of formula I may be used in conjunction with other antimicrobials.

The compound of formula I is also useful as an intermediate for the production of γ-chloroacetoacetic acid derivatives. It is known that γ-chloroacetoacetic acid derivatives, such as esters and arylamides, can be prepared from γ-chloroacetoacetyl chloride and are useful as intermediates e.g. for pigments and dyes.

An example of the use of γ-chloroacetoacetic ester for the preparation of pigments is described in Liebigs Annalen, 313, 12–13, (1900) and Swiss Pat. No. 582,218 in which γ-chloroacetoacetic ester is reacted with a diazotised aromatic amine to give the corresponding arylhydrazone derivative, which, on heating with aqueous alkali, leads to cyclisation und hydrolysis to the pyrazolone carboxylic acid of formula II

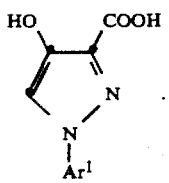

Reaction of II with an aromatic diazonium salt, followed by conversion to the acid chloride, and reaction with a diamine yields pigments of formula III

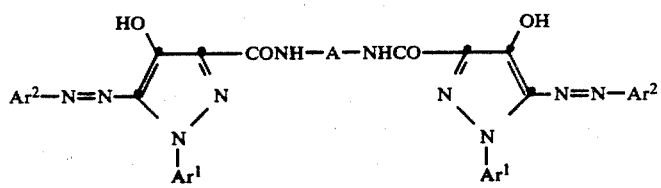

where Ar[1] and Ar[2] are aromatic residues and A is a hydrocarbyl group or a direct bond. However, γ-chloroacetoacetyl chloride is not easily purified and its lack of storage stability necessitates rapid use. By contrast, the compound of formula I is easily purified and storable and so is a more convenient intermediate than γ-chloroacetoacetyl chloride for the production of the above mentioned γ-chloroacetoacetic acid esters and arylamides.

The present invention is further illustrated by the following Examples. Parts and percentages shown therein are by weight.

EXAMPLE 1

2.5 Parts of benzoyl peroxide (containing 25% of water) are suspended in 408 parts of carbon tetrachloride. The mixture is stirred to dissolve the benzoyl peroxide, then dried over magnesium sulphate. To this solution are added 67.5 parts of sulphuryl chloride and the resulting solution is added dropwise over 1¼ hours to a refluxing solution of 42 parts of diketene in 816 parts of carbon tetrachloride. At the end of the addition, the mixture is heated under reflux for a further 1¼ hours, then the carbon tetrachloride is removed on the water pump. Distillation of the residue at 0.01 mb (millibar) gives 4-chloro-4-chloromethyloxetan-2-one, b.p. 35°–36° C., which crystallises on cooling below 20° C. IR$\nu_{max}$. (C=O) 1850 cm$^{-1}$: $^1$H—NMR (CCl$_4$)δ=4.14 (s, 2H, Cl-CH$_2$); 3.82 and 4.20 (both d, 1H, J=17 Hz, H$_2$C(−3).

Analysis: calculated for C$_4$H$_4$Cl$_2$O$_2$: C, 31.00; H,2.60; Cl, 45.75. found: C, 30.51; H,2.51; Cl, 45.45.

Chlorine is bubbled into a solution of 4-chloro-4-chloromethyloxetan-2-one in carbon tetrachloride at 0° C. and the solution so obtained is allowed to stand for several hours. Removal of the carbon tetrachloride and chlorine gives unchanged 4-chloro-4-chlormethyloxetan-2-one.

EXAMPLE 2

A mixture of sulphuryl chloride (13.5 parts), diketene (8.4 parts), benzoyl peroxide (dried, 0.5 parts) and carbon tetrachloride (720 parts) is irradiated by U.V. light at room temperature for 5 hours. The solvent is removed under reduced pressure and the residue is distilled in a Kugelrohr at 50° C. at a pressure of 0.03 mb. The product, 4-chloro-4-chlormethyloxetan-2-one, is obtained as a colourless oil, and is identical with the product obtained in Example 1.

EXAMPLE 3

A mixture of diketene (42.0 parts) and tertiary-butyl-cyclohexylperdicarbonate (6.5 parts) dissolved in carbon tetrachloride (400 parts) is added dropwise over 30 minutes to a refluxing mixture of sulphuryl chloride (67.5 parts) and carbon tetrachloride (800 parts). At the end of the addition, the mixture is refluxed for a further 30 minutes, then the carbon tetrachloride is removed under reduced pressure. Distillation of the residue at 0.03 mb gives 4-chloro-4-chloromethyloxetan-2-one, b.p. 42°–46° C., identical to the product in Example 1.

EXAMPLE 4

A carbon tetrachloride solution containing 42 parts of diketene, 6 parts of bis-(t-butylcyclohexyl)perdicarbonate and 67.5 parts of sulphuryl chloride is pumped through a two vessel cascade at such a rate as to give a residence time of 75 minutes. The residence time is expressed as $$\frac{\text{Vessel volume}}{\text{Volume pumped per minute}}$$

The vessels are stirred vigorously and heated at reflux temperature. The product stream contains 4-chloro-4-chloromethyloxetan-2-one. The carbon tetrachloride is distilled off on a rotary evaporator and the crude product purified by distillation on a wiped wall still to give 4-chloro-4-chloromethyloxetan-2-one identical to the product obtained in Example 1.

EXAMPLE 5

A mixed culture of *Pseudomonas aeruginosa, Enterobacter aerogenes, Escherichia coli, Proteus vulgaris, Bacillus mycoides* and *Staphylococcus aureus* in saline containing 10$^7$ organisms/ml is treated with 30 ppm of the product of Example 1. After one hour the number of organisms is reduced to 10$^2$ organisms/ml, thus demonstrating the rapid bactericidal activity of the product of Example 1.

EXAMPLES OF USE AS INTERMEDIATE FOR PREPARATION OF γ-CHLORO-ACETOACETIC ACID DERIVATIVES

EXAMPLE 6

7.8 Parts of 4-chloro-4-chloromethyloxetan-2-one are dissolved in 200 parts of methanol containing 4.2 parts of anhydrous sodium bicarbonate. After stirring for 20 hours at room temperature, the solids are filtered off, the filtrate is evaporated and the residue distilled to give methyl-γ-chloroacetoacetate, b.p. 48°–50° C./0.8 mb.

EXAMPLE 7

7.8 Parts of 4-chloro-4-chloromethyloxetan-2-one are dissolved in 150 parts of methylenechloride containing 4.2 parts of anhydrous sodium bicarbonate and the solution is cooled to 0° C. 4.7 Parts of aniline are then added over 30 minutes and the reaction mixture is finally stirred for 48 hours at room temperature. The solids are then filtered off and the filtrate evaporated. The residue is crystallised twice from chloroform to give γ-chloroacetoacetanilide, m.p. 142°–143° C.

EXAMPLE 8

7.8 Parts of 4-chloro-4-chloromethyloxetan-2-one are dissolved in 150 parts of methylenechloride containing 4.2 parts of anhydrous sodium bicarbonate and the mixture is cooled to 0° C. 5.4 Parts of p-toluidine in 50 parts of methylenechloride are added over 30 minutes, then the reaction mixture is allowed to warm to room temperature and is stirred at this temperature for 48 hours. The solids are filtered off, washed well with water to remove inorganics and recrystallised from ethanol to give γ-chloro-acetacet-p-toluidide, m.p. 159°–160° C.

What we claim is:

1. A process for producing 4-chloro-4-chloromethyloxetan-2-one, comprising reacting diketene with sulphuryl chloride under conditions in which free radicals are formed.

2. A process according to claim 1 wherein the free radicals are formed by the application to the reaction mixture of ionising radiation or of ultraviolet radiation.

3. A process according to claim 1 wherein the reaction is effected in the presence of a chemical compound capable of forming free radicals.

4. A process according to claim 1 wherein the reaction is effected in the presence of an organic peroxide optionally in conjunction with exposure to ultraviolet radiation or a metal ion catalyst; an inorganic peroxy compound optionally in conjunction with a metal ion catalyst; or an organic azo compound, optionally in conjunction with exposure to ultraviolet radiation.

5. A process according to claim 1 wherein the reaction is effected in the presence of t-butyl peracetate, t-butyl perbenzoate, acetylperoxide, benzoylperoxide, di-isopropylperdicarbonate, di-t-butylcyclohexylperdicarbonate, di-t-butylperoxide or t-butylhydroperoxide.

6. A process according to claim 1 wherein the reaction is effected in the presence of hydrogen peroxide or ammonium persulphate.

7. A process according to claim 1 wherein the reaction is effected in the presence of azobisisobutyronitrile or azobisisopropane.

8. A process according to claim 4 wherein the metal ion catalyst is copper, vanadium, iron or titanium.

9. A process according to claim 1 wherein the reaction is effected in the presence of from 0.1 to 10 mol.%, based on the amount used of diketene, of a compound capable of forming free radicals.

10. A process according to claim 1 wherein the reaction is effected in the presence of from 1 to 5 mol.%, based on the amount used of diketene, of a compound capable of forming free radicals.

11. A process according to claim 1 wherein the reaction is effected in the presence of a solvent which is inert under the reaction conditions.

12. A process according to claim 1 wherein the reaction is effected at a temperature within the range of from 0° to 100° C.

* * * * *